US009778197B2

(12) United States Patent
Bond et al.

(10) Patent No.: US 9,778,197 B2
(45) Date of Patent: Oct. 3, 2017

(54) METAL-DIELECTRIC-CNT NANOWIRES FOR SURFACE-ENHANCED RAMAN SPECTROSCOPY

(71) Applicants: Lawrence Livermore National Security, LLC, Livewrmore, CA (US); ETH Zurich, Zurich (CH)

(72) Inventors: Tiziana C. Bond, Livermore, CA (US); Ali Altun, Zurich (CH); Hyung Gyu Park, Zurich (CH)

(73) Assignees: Lawrence Livermore National Security, LLC, Livermore, CA (US); ETH Zurich, Zurich (CH)

( * ) Notice: Subject to any disclaimer, the term of this patent is extended or adjusted under 35 U.S.C. 154(b) by 70 days.

(21) Appl. No.: 14/450,633

(22) Filed: Aug. 4, 2014

(65) Prior Publication Data
US 2015/0036132 A1 Feb. 5, 2015

Related U.S. Application Data

(60) Provisional application No. 61/862,405, filed on Aug. 5, 2013.

(51) Int. Cl.
*C23C 16/26* (2006.01)
*C23C 16/06* (2006.01)
(Continued)

(52) U.S. Cl.
CPC ......... *G01N 21/658* (2013.01); *C23C 16/045* (2013.01); *C23C 16/405* (2013.01);
(Continued)

(58) Field of Classification Search
CPC .............................. G01N 21/658; C21C 16/26
See application file for complete search history.

(56) References Cited

U.S. PATENT DOCUMENTS 6,504,292 B1 * 1/2003 Choi ...................... H01J 1/304
313/309
7,450,227 B2 11/2008 Dwight et al.
(Continued)

OTHER PUBLICATIONS

Altun et al. "Metal-Dielectric-CNT Nanowires for Femtomolar Chemical Detection by Surface Enhanced Raman Spectroscopy" Adv. Mater. 2013, 25, 4431-4436 May 21, 2013.*
(Continued)

*Primary Examiner* — Kara E Geisel
*Assistant Examiner* — Dominic J Bologna
(74) *Attorney, Agent, or Firm* — Eddie E. Scott

(57) ABSTRACT

A sensor with a substrate includes nanowires extending vertically from the substrate, a hafnia coating on the nanowires that provides hafnia coated nanowires, and a noble metal coating on the hafnia coated nanowires. The top of the hafnia and noble metal coated nanowires bent onto one another to create a canopy forest structure. There are numerous randomly arranged holes that let through scattered light. The many points of contact, hot spots, amplify signals. The methods include the steps of providing a Raman spectroscopy substrate, introducing nano crystals to the Raman spectroscopy substrate, growing a forest of nanowires from the nano crystals on the Raman spectroscopy substrate, coating the nanowires with hafnia providing hafnia coated nanowires, and coating the hafnia coated nanowires with a noble metal or other metal.

7 Claims, 4 Drawing Sheets

(51) Int. Cl.
  *C23C 16/455*   (2006.01)
  *G01N 21/03*    (2006.01)
  *G01N 21/65*    (2006.01)
  *C30B 25/18*    (2006.01)
  *C30B 29/60*    (2006.01)
  *C23C 16/04*    (2006.01)
  *C23C 16/40*    (2006.01)
  *C30B 29/16*    (2006.01)

(52) U.S. Cl.
  CPC ........ *C23C 16/45555* (2013.01); *C30B 25/18* (2013.01); *C30B 29/16* (2013.01); *C30B 29/60* (2013.01); *C30B 29/602* (2013.01)

(56) References Cited

U.S. PATENT DOCUMENTS

| | | | |
|---|---|---|---|
| 7,985,475 B2* | 7/2011 | Dubrow | B05D 1/185 428/357 |
| 2007/0177139 A1* | 8/2007 | Kamins | G02B 6/107 356/301 |
| 2008/0094621 A1* | 4/2008 | Li | G01N 21/658 356/301 |
| 2008/0174775 A1* | 7/2008 | Moskovits | G01N 21/658 356/301 |
| 2008/0266556 A1* | 10/2008 | Kamins | B82Y 20/00 356/301 |
| 2009/0225310 A1 | 9/2009 | Yang et al. | |
| 2011/0053794 A1* | 3/2011 | Zhang | B01J 19/0046 506/9 |
| 2011/0116089 A1* | 5/2011 | Schmidt | G01N 21/658 356/301 |
| 2011/0136288 A1* | 6/2011 | Duane | H01L 21/02381 438/59 |
| 2011/0166045 A1* | 7/2011 | Dhawan | B82Y 10/00 506/39 |
| 2012/0081703 A1* | 4/2012 | Moskovits | G01N 21/658 356/301 |
| 2014/0081150 A1 | 3/2014 | Chu et al. | |

OTHER PUBLICATIONS

Ali Ozhan Altun et al., "Metal-Dietectric-CNT Nanowires for Femtomular Chemical Detection by Surface Enhanced Raman Spectroscopy," Advanced Material, vol. 25, pp. 4431-4436 (2013).

* cited by examiner

METAL-DIELECTRIC-CNT NANOWIRES FOR SURFACE-ENHANCED RAMAN SPECTROSCOPY

CROSS-REFERENCE TO RELATED APPLICATIONS

This application claims priority to and benefit under 35 U.S.C. §119(e) of U.S. Provisional Patent Application No. 61/862,405 filed Aug. 5, 2013 entitled "Reusable Template Based on Metal-Dielectric-CNT Nanowires for Surface-Enhanced Sensitivity," the content of which is hereby incorporated by reference in its entire for all purposes.

STATEMENT AS TO RIGHTS TO APPLICATIONS MADE UNDER FEDERALLY SPONSORED RESEARCH AND DEVELOPMENT

The United States Government has rights in this application pursuant to Contract No. DE-AC52-07NA27344 between the United States Department of Energy and Lawrence Livermore National Security, LLC for the operation of Lawrence Livermore National Laboratory.

BACKGROUND

Field of Endeavor

The present application relates to Raman spectroscopy and more particularly to surface-enhanced Raman spectroscopy (SERS).

State of Technology

This section provides background information related to the present disclosure which is not necessarily prior art.

Surface enhanced Raman spectroscopy (SERS) has attracted considerable interest since its discovery and highlighted single-molecule detection. This interesting phenomenon has been primarily explained by two theories: electromagnetic effect and chemical effect. The chemical enhancement theory is explained through charge transfer complex formation that requires a chemical bond between the molecule and the surface. Electromagnetic enhancement theory, on the other hand, is associated with a local electromagnetic field enhanced by excited surface plasmons on a metal surface, featured by the fourth power field enhancement. The main objective for many researchers has been to fabricate a substrate that can provide a large number of sites of strong field enhancement, so called hotspots. Methods of achieving this target involve localization (sharp tips), coupling (narrow or slightly touching gaps), and resonance (regularity of the metal structure) of surface plasmons, practically enabled by advanced nanomanufacturing techniques.

SUMMARY

Features and advantages of the disclosed apparatus, systems, and methods will become apparent from the following description. Applicant is providing this description, which includes drawings and examples of specific embodiments, to give a broad representation of the apparatus, systems, and methods. Various changes and modifications within the spirit and scope of the application will become apparent to those skilled in the art from this description and by practice of the apparatus, systems, and methods. The scope of the apparatus, systems, and methods is not intended to be limited to the particular forms disclosed and the application covers all modifications, equivalents, and alternatives falling within the spirit and scope of the apparatus, systems, and methods as defined by the claims.

Applicant's apparatus, systems, and methods provide a sensor that greatly amplifies the sensitivity of commonly used but typically weak vibrational spectroscopic methods, such as Raman spectroscopy. This type of sensor makes it possible to detect molecules present in the tiniest of concentrations.

In various embodiments Applicant's methods include the steps of providing a Raman spectroscopy substrate, introducing nano crystals to the Raman spectroscopy substrate, growing a forest of nanowires from the nano crystals on the Raman spectroscopy substrate, coating the nanowires with hafnia providing hafnia coated nanowires, and coating the hafnia coated nanowires with a noble metal or other metal.

In various embodiments Applicant's Raman spectroscopy substrate apparatus includes a Raman spectroscopy substrate, nanowires extending vertically from the Raman spectroscopy substrate, a hafnia coating on the nanowires that provides hafnia coated nanowires, and a noble metal coating on the hafnia coated nanowires. The top of the nanoforest of the hafnia and noble metal coated nanowires does not end up with entirely vertical tips but rather with a canopy of CNTs bent onto one another to create numerous junctions. Such a canopy forest structure offers a great template for a SERS substrate. The crossings of nanowires (or kissing nanowires) leads to superior SERS performance. The tips of the CNTs are sharply curved. There are numerous randomly arranged holes that let through scattered light, and the many points of contact—the 'hot spots'—amplify the signals.

Applicant's apparatus, systems, and methods have use in defense, environmental and pollution monitoring, chem-bio detection, energy harnessing, batteries, capacitors, photovoltaics, surface chemistry monitoring and controls, water filtration, biomedical, and biomedical and applications.

The apparatus, systems, and methods are susceptible to modifications and alternative forms. Specific embodiments are shown by way of example. It is to be understood that the apparatus, systems, and methods are not limited to the particular forms disclosed. The apparatus, systems, and methods cover all modifications, equivalents, and alternatives falling within the spirit and scope of the application as defined by the claims.

BRIEF DESCRIPTION OF THE DRAWINGS

The accompanying drawings, which are incorporated into and constitute a part of the specification, illustrate specific embodiments of the apparatus, systems, and methods and, together with the general description given above, and the detailed description of the specific embodiments, serve to explain the principles of the apparatus, systems, and methods.

DETAILED DESCRIPTION OF SPECIFIC EMBODIMENTS

Figure 1:
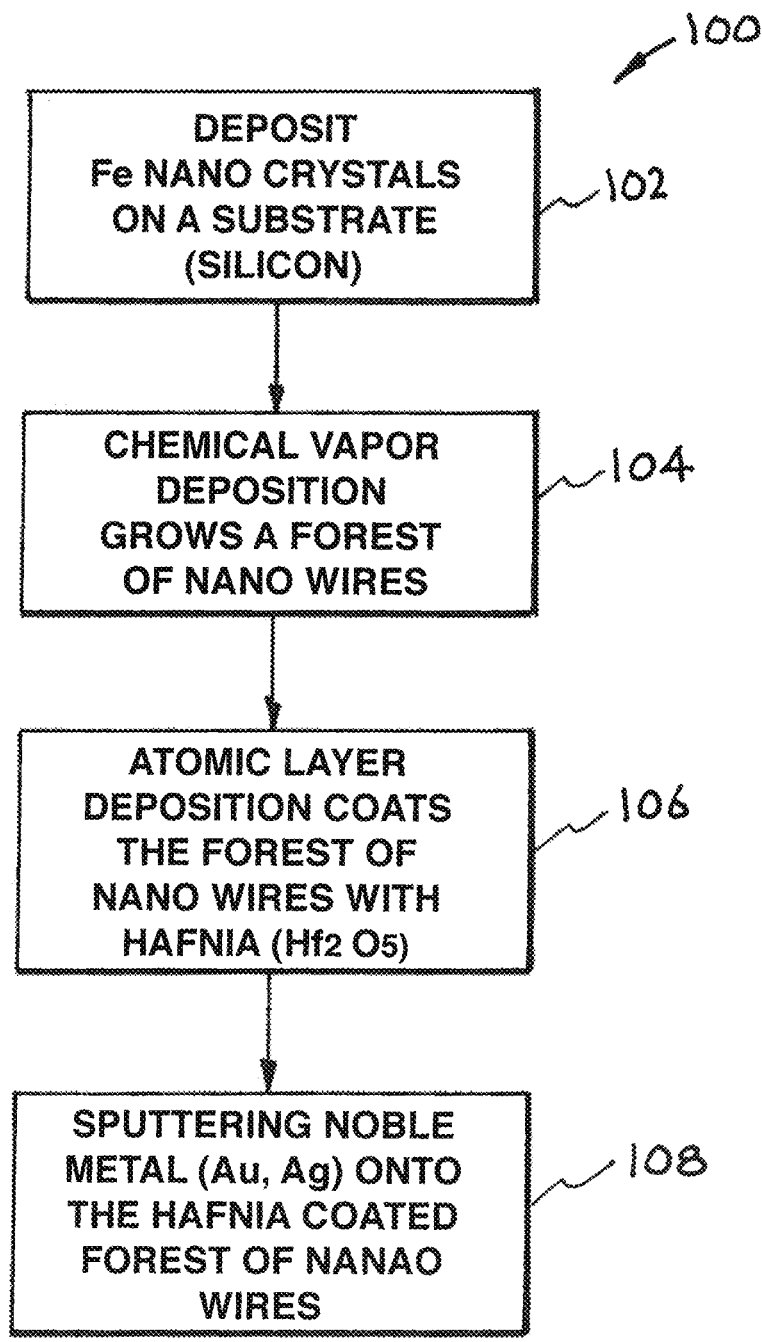
FIG. 1 illustrates one embodiment of Applicant's apparatus, systems, and methods.

Referring to the drawings, to the following detailed description, and to incorporated materials, detailed information about the apparatus, systems, and methods is provided including the description of specific embodiments. The detailed description serves to explain the principles of the apparatus, systems, and methods. The apparatus, systems, and methods are susceptible to modifications and alternative forms. The application is not limited to the particular forms disclosed. The application covers all modifications, equivalents, and, alternatives falling within the spirit and scope of the apparatus, systems, and methods as defined by the claims.

Applicant's apparatus, systems, and methods provide a surface enhanced Raman spectroscopy (SERS) substrate based on a metal-dielectric-CNT nanowire structure. Applicants fabricated a highly sensitive substrate for surface enhanced Raman spectroscopy (SERS) enabled by arrays of gold coated vertically aligned (VA-) carbon nanowires (CNTs) having high-k dielectric (hafnia, $HfO_2$) layer in between as a potential barrier. Applicant's substrate for surface enhanced Raman spectroscopy provided a demonstration of femtomolar-level detection sensitivity and repeated use. Applicants have found, that a nanometer thick layer of hafnia inserted between gold and CNT and random stacks of the gold-hafnia-CNT nanowires are sufficient to enhance the SERS detection performance considerably, demonstrated by femtomolar detection of BPE. The term "nanowires" as used in this application means nanowires and other forms of nano structures including nanotubes.

Referring now to the drawings and in particular to FIG. 1, one embodiment of Applicant's apparatus, systems, and methods is illustrated. This embodiment of Applicant's apparatus, systems, and methods is designated generally by the reference numeral 100. FIG. 1 is a flow chart illustrating this embodiment 100 of the making of a surface enhanced Raman spectroscopy substrate.

In step 102 iron nanoparticles (average sizes between one and two nanometers) are deposited on a silicon substrate coated with aluminum oxide (with thickness between ten and twenty nanometers). It is to be understood that substrates other than silicon substrates are contemplated in the apparatus, systems, and methods of this application. Other substrates include but are not limited to aluminum oxide substrates, glass substrates and other substrates. It is to be understood that nanoparticles of the species other than iron are contemplated in the apparatus, systems, and methods of this application. Other nanoparticles include but are not limited to nickel nanoparticies, platinum nanoparticles and other nano crystals.

In step 104 chemical vapor deposition (CVD) is used to grow a forest of nanowires from the nano crystals on the substrate. Chemical vapor deposition is a process where solids form out of a gaseous phase and the nanowires are grown from the nano crystals on the substrate. It is to be understood that other metals can be used as the nano crystals and that other methods can be used for growing the nanowires from the nano crystals on the substrate. For example, sputtering and e-beam evaporation methods can be used for growing the nanowires from the nano crystals on the substrate.

In step 106 the nanowires are coated with hafnia by atomic layer deposition. In step 108 the hafnia coated nanowires are coated with a noble metal, for example gold. Applicants introduced atomic layer deposition (ALD) of hafnia on CNT samples prior to the gold evaporation. Hafnia in particular was selected due to its high dielectric constant and bandgap ($\in r=25$, E b=6 eV). In Applicants embodiment 100, VA-CNT substrates were conformally coated with hafnia of various thicknesses and then coated with gold of various thicknesses in order to optimize the SERS effect created by the CNT array template via suppression of plasmon leakage.

The very top part of Applicant's hafnia-gold coated nanowires has a canopy of bent nanowires and the resultant structure resembles a horizontally or obliquely stacked gold-hafnia-CNT nanowires. Applicants found that there exists optimal gold thickness of 10.5-21 nm that, along with the dielectric insert of hafnia, allows for the best SERS performance. The estimated total gold-hafnia-CNT nanowire thickness lies between 35 nm and 56 nm).

The top of the nanoforest does not end up with entirely vertical tips but rather with a canopy of CNTs bent onto one another to create numerous functions. Such a canopy forest structure offers a great template for a SERS substrate when coated with noble metal. The crossings of nanowires (or kissing nanowires) leads to superior SERS performance. The bent tips of the dense VA-CNT array enables the kissing nanowire effect when coated with an optimal thickness of noble metal.

Applicant's apparatus, systems, and methods 100 have use in defense, environmental and pollution monitoring, chem-bio detection, energy harnessing, batteries, capacitors, photovoltaics, surface chemistry monitoring and controls, water filtration, biomedical, and biomedical and applications. Applicant's vertically aligned (VA) carbon nanowires (CNTs) offers an extremely dense and rough nanostructure as a viable template for the SERS substrate. This nanoforest of VA-CNTs is particularly attractive, since it provides vertical arrays of nanowires with a variety of diameters from tens of angstroms to hundreds of nanometers.

Figure 2:
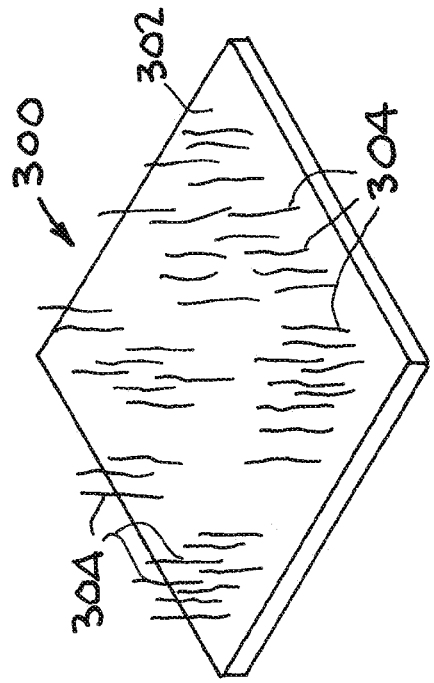
FIG. 2 shows a substrate with nano crystals.

Referring now to FIG. 2, additional embodiments of Applicant's apparatus, systems, and methods are illustrated. The additional embodiments of Applicant's apparatus, systems, and methods provide methods of making a substrate for surface enhanced Raman spectroscopy that include the steps of providing a Raman spectroscopy substrate, introducing nano crystals to the Raman spectroscopy substrate, growing a forest of nanowires from the nano crystals on the Raman spectroscopy substrate, coating the nanowires with hafnia providing hafnia coated nanowires, and coating the hafnia coated nanowires with a noble metal. The methods produce a surface enhanced Raman spectroscopy substrate apparatus that includes a Raman spectroscopy substrate, nanowires extending vertically from the Raman spectroscopy substrate, a hafnia coating on the nanowires that provides hafnia coated nanowires, and a noble metal coating on the hafnia coated nanowires. One of the additional embodiments is illustrated in FIG. 2 and is designated generally by the reference numeral 200.

As shown in FIG. 2 a substrate 202 is provided. The substrate 202 can be a silicon substrate or a substrate of other material. Iron nano crystals 204 or other nano crystals are introduced to the substrate 202. It is to be understood that FIG. 2 is not to scale and that the nano crystals 204 are shown greatly enlarged for illustration purposes.

Figure 3:
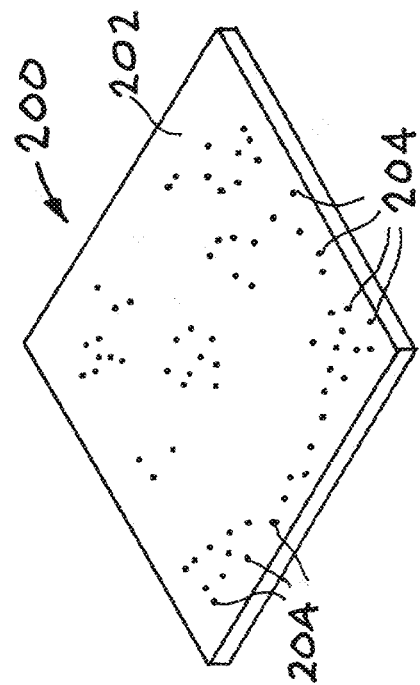
FIG. 3 shows a substrate with a forest of nanowires.

Referring now to FIG. 3, additional embodiments of Applicant's apparatus, systems, and methods are illustrated. The additional embodiment illustrated is designated generally by the reference numeral 300. As shown in FIG. 3 a substrate 302 is provided. The substrate 302 can be a silicon substrate or a substrate of other material. Chemical vapor deposition was used to grow a forest of nanowires 304 on the substrate 302. The nanowires 304 were coated with hafnia by atomic layer deposition and the hafnia coated nanowires 304 were coated with a noble metal, for example gold. It is to be understood that FIG. 3 is not to scale and that the nanowires 304 are shown greatly enlarged for illustration purposes.

Figure 4:
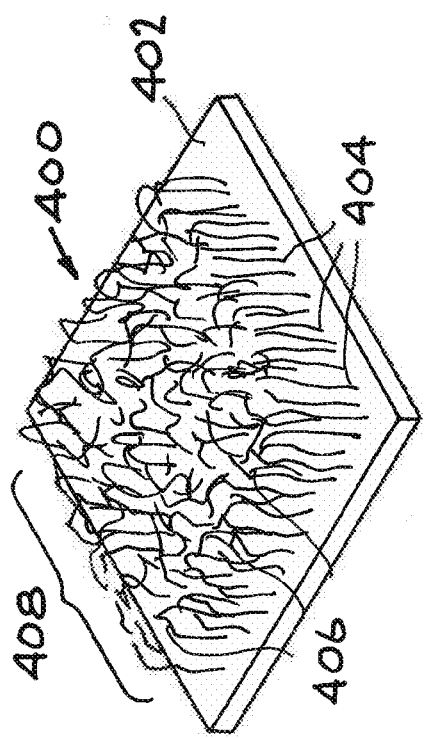
FIG. 4 shows a substrate with a forest of nanowires and the very top part of the nanowires has a canopy of bent nanowires.

Referring now to FIG. 4, additional embodiments of Applicant's apparatus, systems, and methods are illustrated. The additional embodiment illustrated is designated generally by the reference numeral 400. As shown in FIG. 4 a substrate 402 is provided. The substrate 402 can be a silicon substrate or a substrate of other material. Chemical vapor deposition was used to grow a forest of nanowires 404 on the substrate 402. The nanowires 404 were coated with hafnia by atomic layer deposition and the hafnia coated nanowires 404 were coated with a noble metal or other metal. The hafnia coated nanowires 404 can be coated with aluminum, silver, gold, and various noble metals.

The very top part 406 of Applicant's hafnia-gold coated nanowires 404 produces a canopy 408 of bent nanowires. The resultant structure, is a canopy of horizontally or obliquely stacked gold-hafnia-CNT nanowires. Applicants found that there exists optimal gold thickness of 10.5-21 nm that, along with the dielectric insert of hafnia, allows for the best SERS performance. The estimated total gold-hafnia-CNT nanowire thickness lies between 35 nm and 56 nm. It is to be understood that FIG. 4 is not to scale and that the nanowires 404, the top part 406 the nanowires 404, and the canopy 408 are shown greatly enlarged for illustration purposes.

Figure 5:
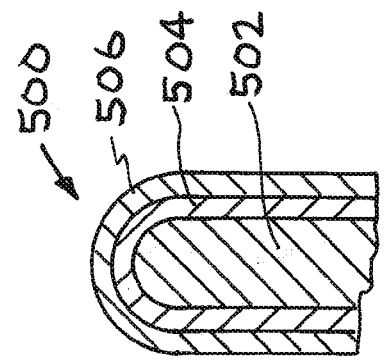
FIG. 5 shows a cross section of a nanowire with hafina and gold coatings.

Referring now to FIG. 5, a cross section of a nanowire with hafnia and gold coatings is illustrated. The additional embodiment illustrated is designated generally by the reference numeral 500. The nanowires 502 are shown coated with hafnia 504 and the hafnia coated nanowires are shown coated with a noble metal, for example gold 506. It is to be understood that FIG. 5 is not to scale and that the nanowires 502 are shown greatly enlarged for illustration purposes.

Applicant's apparatus, systems, and methods provide a substrate for surface enhanced Raman spectroscopy. The methods include the steps of providing a Raman spectroscopy substrate, introducing nano crystals to the Raman spectroscopy substrate, growing a forest of nanowires from the nano crystals on the Raman spectroscopy substrate, coating the nanowires with hafnia providing hafnia coated nanowires, and coating the hafnia coated nanowires with a noble metal. The methods produce a surface enhanced Raman spectroscopy substrate apparatus that includes a Raman spectroscopy substrate, nanowires extending vertically from the Raman spectroscopy substrate, a hafnia coating on the nanowires that provides hafnia coated nanowires, and a noble metal coating on the hafnia coated nanowires.

Referring again to FIG. 4 a surface enhanced Raman spectroscopy substrate apparatus that is produced by the methods is shown. The top 406 of the nanoforest of the hafnia and noble metal coated nanowires 404 does not end up with entirely vertical tips but rather with a canopy 408 of CNTs bent onto one another to create numerous junctions. Such a canopy forest 408 structure offers a great template for a SERS substrate. The crossings of nanowires (or kissing nanowires) leads to superior SERS performance. The bent tips of the dense VA-CNT array enables the kissing nanowire effect when coated with an optimal thickness of noble metal.

The top of the nanoforest provides a canopy 408 of CNTs bent onto one another to create numerous junctions. The tips 406 of the CNTs 404 are sharply curved. The point of contact between the surface of the canopy 408 and the sample resembles a plate of spaghetti. However, between the strands of spaghetti, there are numerous randomly arranged holes that let through scattered light and the many points of contact—the 'hot spots'—amplify the signals. The nanospaghetti structure with metal-coated CNT tips is perfect for maximizing the density of these contact points. The wide distribution of metallic nano-crevices in the nanometer range, well recognized to be responsible for extreme electromagnetic enhancement (or hot spots) and highly pursued by many research groups, has been easily and readily achieved by Applicants, resulting in the intense and reproducible enhancements.

Applicant's apparatus, systems, and methods have use in defense, defense, environmental and pollution monitoring, chem-bio detection, energy harnessing, batteries, capacitors, photovoltaics, surface chemistry monitoring and controls, water filtration, biomedical, and biomedical and applications. Applicant's vertically aligned (VA) carbon nanowires (CNTs) offers an extremely dense and rough nanostructure as a viable template for the SERS substrate. This nanoforest of VA-CNTs is particularly attractive, since it provides vertical arrays of nanowires with a variety of diameters from tens of angstroms to hundreds of nanometers.

Figure 6:
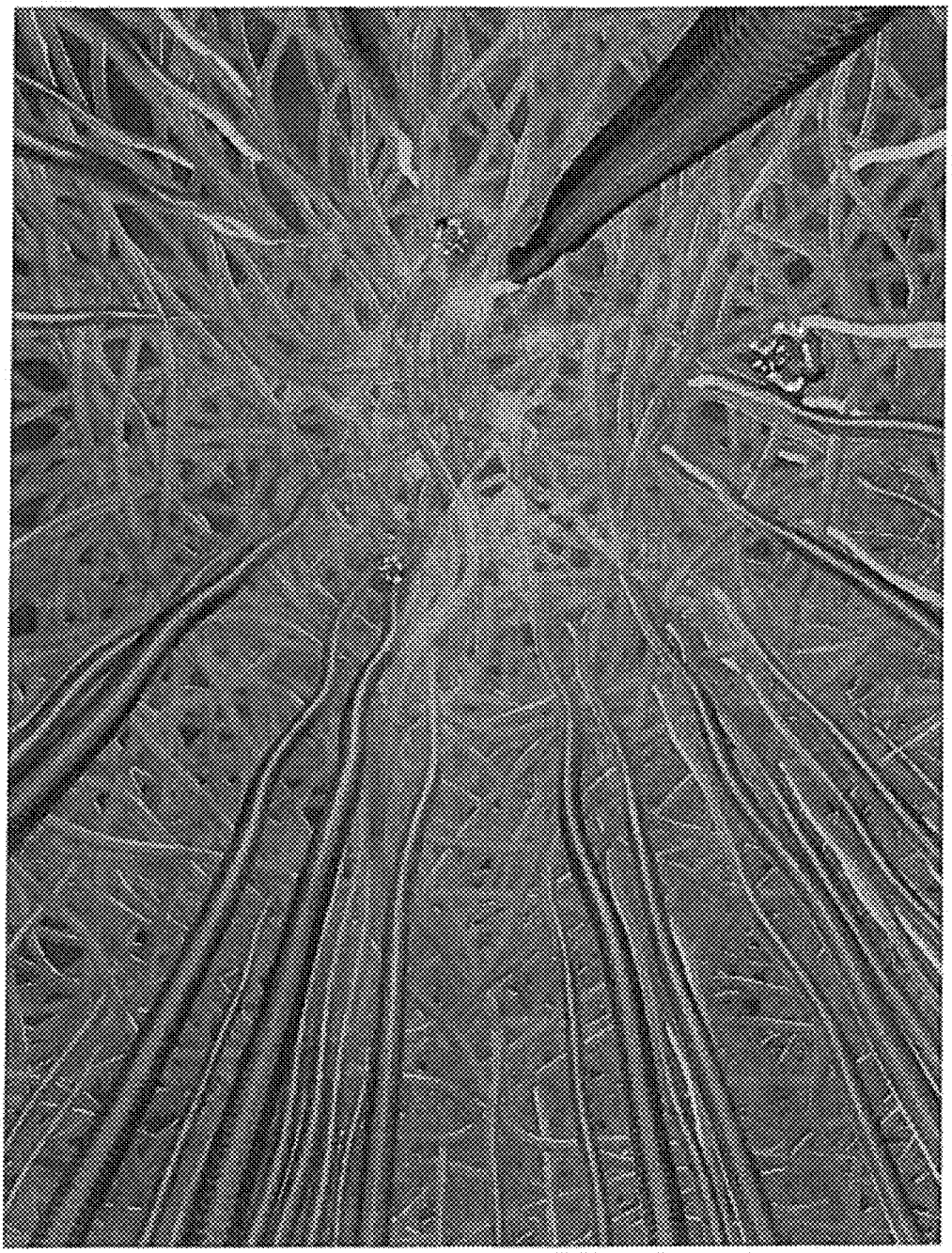
FIG. 6 is an illustration of the carbon nanotubes having curved tips with numerous gaps to let through the Raman scattered light that is an important feature of Applicant's high-sensitivity sensor.

Applicant's apparatus, systems, and methods provide a sensor that greatly amplifies the sensitivity of commonly used but typically weak vibrational spectroscopic methods, such as Raman spectroscopy. This type of sensor makes it possible to detect molecules present in the tiniest of concentrations. Referring now to FIG. 6 the carbon nanotubes having curved tips with numerous gaps to let through the Raman scattered light that is an important feature of Applicant's high-sensitivity sensor are illustrated.

FIG. 6 is a view from inside Applicant's surface-enhanced Raman spectroscopy structure looking upward from the base of the structure. The long squiggly darker lines are the nano wires as grown by the chemical vapor deposition step 104 described above and illustrated in FIG. 1. The nanowires extend vertically from the Raman spectroscopy substrate. The hafnia coating on the nanowires provides hafnia coated nanowires and there is a noble metal coating on the hafnia coated nanowires. The top of the nanoforest of the hafnia and noble metal coated nanowires does not end up with entirely vertical tips but rather with a canopy of CNTs bent onto one another to create numerous junctions. Such a canopy forest structure offers a great template for a SERS substrate.

The inventors conducted experiments that support the inventor's Raman spectroscopy substrate having nanowires extending vertically from the Raman spectroscopy substrate, a hafnia coating on the nanowires that provides hafnia coated nanowires, a noble metal coating on the hafnia coated nanowires, and bent ends on the nanowires. The bent ends provide a canopy of bent nanowire ends. The canopy of bent nanowire ends includes holes between the bent nanowire ends and includes points of contact of said bent nanowire ends.

VA-CNT samples were prepared by chemical vapor deposition (CVD) using catalysts of I-nm-thick iron atop 20-nm-thick aluminum on 1×1 cm2 silicon substrates. The film was then annealed in a cold wall CVD furnace (Black Magic™, Aixtron) at a temperature of 750° C. for 10 min. The average areal number density of catalyst islands, approximately equivalent to the average areal number density of CNTs, measures 500 μm-2 by atomic force microscopy.

For the CVD process, the catalyst substrate was loaded into the same CVD furnace followed by chamber evacuation below 0.2 mbar. The reactor temperature was held above 100° C. during loading/unloading to minimize moisture condensation. Under a shower head gas flow of hydrogen (200 seem) and Argon (300 seem), the reactor temperature was raised to the growth temperature at a ramp rate of 300° C./min and maintained there for 5 minutes for catalyst reduction while the total chamber pressure was kept at around 6-7 mbar. During the CNT growth step 5 seem of acetylene (C2H2) was added for 15 min at 480 mbar total pressure. Upon completion of the growth step, the reactor was cooled down in Ar. A uniform and dense forest of VA-CNT was synthesized as a mixture of multi and a few walled nanotubes. The length of CNTs is about 40 μm. Most of tips of CNTs were bent.

Since the very top parts of the inventors CNT sample has an irregular network of bent nanotubes, the resultant structure resembles a horizontally or obliquely stacked gold-hafnia-CNT nano wires of less than a few micrometers long. In this structure, the expected role of CNT is a template for the gold nanowire formation. Nevertheless, the CNT may act as an electron sink quenching surface plasmons significantly. Indeed, when gold is directly deposited on the VA-CNT forest without any dielectric barrier, the inventors could observe SERS signal merely at the nano molar level. This result supports the role of the sandwiched high-k dielectric as the quenching barrier of an undesired loss of gold surface plasmons into CNT.

The inventors attribute this strong SERS signal and femtomolar-sensitive detection to the abundance of the gold-hafnia-CNT nanowire junctions per unit area. Some of these junctions can apparently result in strong hotspots as suggested by the previous studies. In combination with the effect of plasmon quenching elimination by high-k dielectric barrier, these nano wire junctions could manifest their use in highly sensitive SERS measurements. Interestingly, the aforementioned sensitive SERS performance was achieved without a visible plasmon resonance of the substrate per se. This absence of plasmon resonance is perhaps due to the random configuration and distribution of gold nanowire junctions at the top part of the inventor's substrate. Accordingly, the inventors study proves that it is possible to construct a SERS substrate that is cheap, uniform and repeatable, requires no lithographic techniques, and can facilitate strong hotspots even without a requirement of plasmon resonance.

Figure 7A:
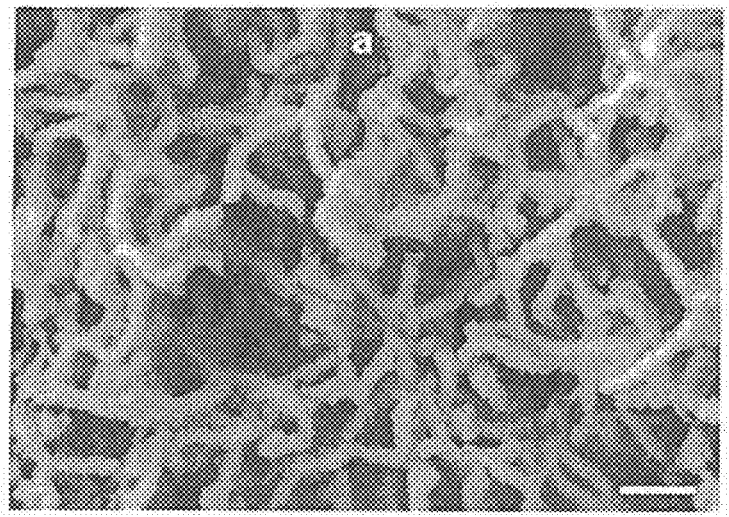
FIG. 7A is SEM image a scale bar: 200 nm of 2.5-nm-thick hafnia and 100-nm-thick gold coated VA-CNT showing nanowires wherein the nanowires have bent ends.
Figure 7B:
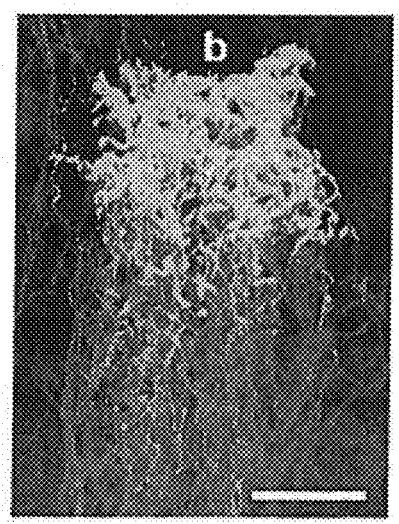
FIG. 7B is a SEM image scale bar: 1 μm of a bundle of 2.5-nm-thick hafnia and 100-nm-thick gold coated V A-CNT showing nanowires wherein the nanowires have bent ends.

Results of the inventors experiments are shown in FIG. 7A and FIG. 7B. FIG. 7A is SEM image a scale bar: 200 nm of 2.5-nm-thick hafnia and 100-nm-thick gold coated VA-CNT showing nanowires wherein the nanowires have bent ends. FIG. 7B is a SEM image scale bar: 1 μm of a bundle of 2.5-nm-thick hafnia and 100-nm-thick gold coated VA-CNT showing nanowires wherein the nanowires have bent ends.

Although the description above contains many details and specifics, these should not be construed as limiting the scope of the application but as merely providing illustrations of some of the presently preferred embodiments of the apparatus, systems, and methods. Other implementations, enhancements and variations can be made based on what is described and illustrated in this patent document. The features of the embodiments described herein may be combined in all possible combinations of methods, apparatus, modules, systems, and computer program products. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Therefore, it will be appreciated that the scope of the present application fully encompasses other embodiments which may become obvious to those skilled in the art. In the claims, reference to an element in the singular is not intended to mean "one and only one" unless explicitly so stated, but rather "one or more." All structural and functional equivalents to the elements of the above-described preferred embodiment that are known to those of ordinary skill in the art are expressly incorporated herein by reference and are intended to be encompassed by the present claims. Moreover, it is not necessary for a device to address each and every problem sought to be solved by the present apparatus, systems, and methods, for it to be encompassed by the present claims. Furthermore, no element or component in the present disclosure is intended to be dedicated to the public regardless of whether the element or component is explicitly recited in the claims. No claim element herein is to be construed under the provisions of 35 U.S.C. 112, sixth paragraph, unless the element is expressly recited using the phrase "means for."

While the apparatus, systems, and methods may be susceptible to various modifications and alternative forms, specific embodiments have been shown by way of example in the drawings and have been described in detail herein. However, it should be understood that the application is not intended to be limited to the particular forms disclosed. Rather, the application is to cover all modifications, equivalents, and alternatives falling within the spirit and scope of the application as defined by the following appended claims.

The invention claimed is:

1. A method of making a substrate for surface enhanced Raman spectroscopy, comprising the steps of:
   providing a Raman spectroscopy substrate,
   introducing nano crystals directly onto said Raman spectroscopy substrate,
   growing a forest of nanowires from said nano crystals that have been introduced directly onto said Raman spectroscopy substrate, said step of growing a forest of nanowires from said nano crystals comprising growing a forest of nanowires extending vertically from said nanocrystals and extending vertically from said Raman spectroscopy substrate wherein said nanowires have vertical sections of said nanowires wherein said vertical sections extend vertically from said Raman spectroscopy substrate and top parts of said nanowires connected to said vertical sections of said nanowires wherein said top parts of said nanowires form bent ends of said nanowires that extend horizontally and parallel to said Raman spectroscopy substrate, coating said nanowires including said vertical sections and said bent ends with hafnia providing hafnia coated nanowires, hafnia coated vertical sections, and hafnia coated bent ends, coating said hafnia coated nanowires with a noble metal providing noble metal and hafnia coated nanowires, noble metal and hafnia coated vertical sections, and noble metal and hafnia coated bent ends, and forming a canopy of said noble metal and hafnia coated bent ends of said noble metal and hafnia coated nanowires that extends horizontally and parallel to said Raman spectroscopy substrate.

2. The method of making a substrate for surface enhanced Raman spectroscopy of claim 1 wherein said step of forming a canopy of said noble metal and hafnia coated bent ends includes allowing holes to be formed between said bent ends.

3. The method of making a substrate for surface enhanced Raman spectroscopy of claim 1 wherein said step of forming a canopy of said noble metal and hafnia coated bent ends includes allowing points of contact of said bent ends to be formed.

4. A surface enhanced Raman spectroscopy substrate apparatus, comprising:

a Raman spectroscopy substrate, nanowires extending vertically from said Raman spectroscopy substrate, wherein said nanowires have vertical sections of said nanowires wherein said vertical sections extend vertically from said Raman spectroscopy substrate and top parts of said nanowires connected to said vertical sections of said nanowires wherein said top parts of said nanowires form bent ends of said nanowires that extend horizontally and parallel to said Raman spectroscopy substrate, a hafnia coating on said nanowires that provides hafnia coated nanowires including hafnia coated vertical sections of said nanowires and hafnia coated bent ends of said nanowires, a noble metal coating on said hafnia coated nanowires that provides noble metal coated hafnia coated vertical sections of said nanowires and noble metal coated hafnia coated bent ends of said nanowires, and a canopy of said noble metal coated hafnia coated bent ends of said nanowires that extend horizontally and parallel to said Raman spectroscopy substrate wherein said noble metal coated hafnia coated bent ends of said nanowires forms said canopy that extend horizontally and parallel to said Raman spectroscopy substrate.

5. The surface enhanced Raman spectroscopy substrate apparatus of claim 4 wherein said canopy of bent ends includes holes between said bent ends.

6. A method of making a substrate for surface enhanced Raman spectroscopy, comprising the steps of:

providing a Raman spectroscopy substrate, introducing nano crystals directly onto said Raman spectroscopy substrate, growing a forest of nanowires from said nano crystals that have been introduced directly onto said Raman spectroscopy substrate, said step of growing a forest of nanowires from said nano crystals comprising growing a forest of nanowires extending vertically from said nanocrystals and extending vertically from said Raman spectroscopy substrate wherein said nanowires have vertical sections of said nanowires wherein said vertical sections extend vertically from said Raman spectroscopy substrate and top parts of said nanowires connected to said vertical sections of said nanowires wherein said top parts of said nanowires form bent ends of said nanowires that extend horizontally and parallel to said Raman spectroscopy substrate, coating said nanowires including said vertical sections and said bent ends with hafnia providing hafnia coated nanowires, hafnia coated vertical sections, and hafnia coated bent ends, coating said hafnia coated nanowires with a gold coating that has a thickness of between ten and one half nanometers and twenty one nanometers providing gold and hafnia coated nanowires, gold and hafnia coated vertical sections, and gold and hafnia coated bent ends with a total gold-hafnia-nanowire thickness that lies between thirty five nanometers and fifty six nanometers, forming a canopy of said gold and hafnia coated bent ends of said gold and hafnia coated nanowires that extends horizontally and parallel to said Raman spectroscopy substrate, forming a multiplicity of holes in said canopy extending from said canopy toward said Raman spectroscopy substrate where said multiplicity of holes are located between said gold coated hafnia coated vertical sections of said nanowires, and forming many points of contact between said gold coated hafnia coated vertical sections of said nanowires located in said multiplicity of holes wherein said many points of contact provide electromagnetic enhancement.

7. A surface enhanced Raman spectroscopy substrate apparatus, comprising:

a Raman spectroscopy substrate, nanowires extending vertically from said Raman spectroscopy substrate, wherein said nanowires have vertical sections of said nanowires wherein said vertical sections extend vertically from said Raman spectroscopy substrate and top parts of said nanowires connected to said vertical sections of said nanowires wherein said top parts of said nanowires form bent ends of said nanowires that extend horizontally and parallel to said Raman spectroscopy substrate, a hafnia coating on said nanowires that provides hafnia coated nanowires including hafnia coated vertical sections of said nanowires and hafnia coated bent ends of said nanowires, a gold coating on said hafnia coated nanowires that has a thickness of between ten and one half nanometers and twenty one nanometers that provides gold coated hafnia coated vertical sections of said nanowires with a total gold-hafnia-nanowire thickness that lies between thirty five nanometers and fifty six nanometers and gold coated hafnia coated bent ends of said nanowires, a canopy of said gold coated hafnia coated bent ends of said nanowires that extend horizontally and parallel to said Raman spectroscopy substrate wherein said gold coated hafnia coated bent ends of said nanowires forms said canopy that extend horizontally and parallel to said Raman spectroscopy substrate,
a multiplicity of holes in said canopy extending from said canopy toward said substrate where said multiplicity of holes are located between said gold coated hafnia coated vertical sections of said nanowires, and
many points of contact between said gold coated hafnia coated vertical sections of said nanowires located in said multiplicity of holes wherein said many points of contact provide electromagnetic enhancement.

\* \* \* \* \*